US007732535B2

(12) United States Patent
Pacetti

(10) Patent No.: US 7,732,535 B2
(45) Date of Patent: Jun. 8, 2010

(54) COATING FOR CONTROLLED RELEASE OF DRUGS FROM IMPLANTABLE MEDICAL DEVICES

(75) Inventor: Stephen D. Pacetti, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 587 days.

(21) Appl. No.: 11/088,501

(22) Filed: Mar. 23, 2005

(65) Prior Publication Data

US 2005/0187376 A1 Aug. 25, 2005

Related U.S. Application Data

(63) Continuation-in-part of application No. 10/236,366, filed on Sep. 5, 2002, now abandoned.

(51) Int. Cl.
C08C 19/25 (2006.01)
C08C 19/14 (2006.01)
C08C 19/20 (2006.01)
C08C 19/22 (2006.01)
C08F 8/24 (2006.01)
C08F 8/30 (2006.01)
C08F 8/34 (2006.01)

(52) U.S. Cl. .......... 525/342; 525/60; 525/343; 525/353; 525/359.3; 525/359.5; 524/557; 623/1.42; 424/400; 427/2.24

(58) Field of Classification Search ............... 525/60, 525/61, 342, 353, 359.3, 359.5, 343; 524/557; 623/1.42, 1.43; 424/400; 427/2.24
See application file for complete search history.

(56) References Cited

U.S. PATENT DOCUMENTS

| | | | |
|---|---|---|---|
| 2,072,303 A | 3/1937 | Herrmann et al. | |
| 4,733,665 A | 3/1988 | Palmaz | |
| 4,800,882 A | 1/1989 | Gianturco | |
| 4,886,062 A | 12/1989 | Wiktor | |
| 4,977,901 A | 12/1990 | Ofstead | |
| 5,112,457 A | 5/1992 | Marchant | |
| 5,328,471 A | 7/1994 | Slepian | |
| 5,349,023 A * | 9/1994 | Ikeda et al. ............ | 525/61 |
| 5,455,040 A | 10/1995 | Marchant | |
| 5,464,650 A | 11/1995 | Berg et al. | |
| 5,578,073 A | 11/1996 | Haimovich et al. | |
| 5,605,696 A | 2/1997 | Eury et al. | |
| 5,628,730 A | 5/1997 | Shapland et al. | |
| 5,667,767 A | 9/1997 | Greff et al. | |
| 5,670,558 A | 9/1997 | Onishi et al. | |
| 5,700,286 A | 12/1997 | Tartaglia et al. | |
| 5,716,981 A | 2/1998 | Hunter et al. | |
| 5,800,392 A | 9/1998 | Racchini | |
| 5,824,049 A | 10/1998 | Ragheb et al. | |
| 5,830,178 A | 11/1998 | Jones et al. | |
| 5,837,313 A | 11/1998 | Ding et al. | |
| 5,851,508 A | 12/1998 | Greff et al. | |
| 5,858,746 A | 1/1999 | Hubbell et al. | |
| 5,865,814 A | 2/1999 | Tuch | |
| 5,873,904 A | 2/1999 | Ragheb et al. | |
| 5,971,954 A | 10/1999 | Conway et al. | |
| 5,980,928 A | 11/1999 | Terry | |
| 5,980,972 A | 11/1999 | Ding | |
| 5,997,517 A | 12/1999 | Whitbourne | |
| 6,010,530 A | 1/2000 | Goicoechea | |
| 6,015,541 A | 1/2000 | Greff et al. | |
| 6,042,875 A | 3/2000 | Ding et al. | |
| 6,051,648 A | 4/2000 | Rhee et al. | |
| 6,056,993 A | 5/2000 | Leidner et al. | |
| 6,060,451 A | 5/2000 | DiMaio et al. | |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,113,629 A | 9/2000 | Ken | |
| 6,120,536 A | 9/2000 | Ding et al. | |
| 6,120,904 A | 9/2000 | Hostettler et al. | |
| 6,121,027 A | 9/2000 | Clapper et al. | |
| 6,129,761 A | 10/2000 | Hubbell | |
| 6,153,252 A | 11/2000 | Hossainy et al. | |
| 6,165,212 A | 12/2000 | Dereume et al. | |
| 6,258,121 B1 | 7/2001 | Yang et al. | |
| 6,287,628 B1 | 9/2001 | Hossainy et al. | |
| 6,379,381 B1 | 4/2002 | Hossainy et al. | |
| 6,503,954 B1 | 1/2003 | Bhat et al. | |
| 2001/0037145 A1 | 11/2001 | Guruwaiya et al. | |

FOREIGN PATENT DOCUMENTS

| | | |
|---|---|---|
| EP | 0 135 705 | 4/1985 |
| EP | 0 310 856 | 2/1989 |

(Continued)

OTHER PUBLICATIONS

International Search Report for PCT/US2006/010069, filed Mar. 17, 2006, mailed Jul. 3, 2006, 11 pgs.

(Continued)

*Primary Examiner*—Duc Truong
(74) *Attorney, Agent, or Firm*—Squire Sanders & Dempsey LLP

(57) ABSTRACT

A coating for an implantable medical device comprising modified poly(ethylene-co-vinyl alcohol).

14 Claims, No Drawings

FOREIGN PATENT DOCUMENTS

| | | |
|---|---|---|
| EP | 0 665 023 | 8/1995 |
| EP | 0 787 755 | 8/1997 |
| EP | 0 879 595 | 11/1998 |
| EP | 0 970 711 | 1/2000 |
| JP | 10158326 | 6/1998 |
| WO | WO 91/12846 | 9/1991 |
| WO | WO 96/40174 | 12/1996 |
| WO | WO 97/45105 | 12/1997 |
| WO | WO 98/17331 | 4/1998 |
| WO | WO 99/01118 | 1/1999 |
| WO | WO 99/63981 | 12/1999 |
| WO | WO 00/02599 | 1/2000 |
| WO | WO 00/12147 | 3/2000 |
| WO | WO 00/64506 | 11/2000 |
| WO | WO 01/01890 | 1/2001 |
| WO | WO 01/45763 | 6/2001 |
| WO | WO 01/74414 | 10/2001 |
| WO | WO 2004/022119 | 3/2004 |
| WO | WO 2004/101018 | 11/2004 |
| WO | WO 2005/032613 | 4/2005 |

OTHER PUBLICATIONS

Anonymous, *Rolling Therapeutic Agent Loading Device for Therapeutic Agent Delivery or Coated Stent* (Abstract 434009), Res. Disclos. p. 975 (Jun. 2000).

Barath et al; *Low Dose of Antitumor Agents Prevents Smooth Muscle Cell Proliferation After Endothelial Injury* JCAA 13(2):252A (1989).

Dichek et al., *Seeding of Intravascular Stents with Genetically Engineered Endothelial Cells*, Circ. 80(5):1347-1353 (1989).

Herdeg et al., *Antiproliferative Stent Coatings: Taxol and Related Compounds*, Semin. Intervent. Cardiol. 3:197-199 (1998).

Matsumaru et al.; *Embolic Materials for Endovascular Treatment of Cerebral Lesions*, J. Biomater. Sci. Polymer Edn. 8(7):555-569 (1997).

Marconi, W. et al.: *Polymeric Systems Based on Derivatives of Ethylene-Vinyl Alcohol Copolymers*, J. Bioactive Compatible Polymers, vol. 15, May 2000, pp. 257-271.

Miyazaki et al.; *Antitumor effect of Implanted Ethylene-Vinyl Alcohol Copolymer Matrices Containing Anticancer Agents on Ehrlich Ascites Carcinoma and P388 Leukemia in Mice*; Chem. Pharm. Bull. 33(6):2490-2498 (1985).

Miyazawa et al.; *Effects of Pemirolast and Tranilast on Intimal Thickening After Arterial Injury in the Rat*; J. Cardiovasc. Pharmacol., pp. 157-162 (1997).

Ohsawa et al.; *Preventive Effects of an Antiallergic Drug, Pemirolast Potassium, on Restenosis After Percutaneous Transluminal Coronary Angioplasty*; American Heart Journal; pp. 1081-1087 (1998).

Oyane, A. et al.: *Apatite Formation on Ethylene-Vinyl Alcohol Copolymer Modified with Silanol Groups*, RAPRA Abstracts, Pergamon Press Ltd., Oxford, GB, vol. 37, No. 3, Mar. 2000, p. 167 (Abstract).

Shigeno; *Prevention of Cerebrovascular Spasm by Bosentan, Novel Endothelin Receptor*; Chemical Abstract 125:212307 (1996).

Toselli, M. et al.: *Modification of EVOH Copolymers with Epsilon-Caprolactone: Synthesis and Compatibilization Effects in PE/PVC Blends*, Macromolecular Symposia, No. 176, Nov. 2001, pp. 233-244.

\* cited by examiner

COATING FOR CONTROLLED RELEASE OF DRUGS FROM IMPLANTABLE MEDICAL DEVICES

RELATED APPLICATION

This application is a continuation-in-part of application Ser. No. 10/236,366, filed 5 Sep. 2002 now abandoned.

FIELDS

This invention relates to the fields of organic chemistry, medicine, pharmacology, polymer science and medical devices. In particular this invention is related to polymeric coatings useful for controlled localized drug delivery from an implantable medical device and to the medical devices comprising such coatings.

BACKGROUND

A stent is an implantable medical device comprising a tubular scaffold used to mechanically retain the patency of a lumen in which it is placed. Stents may be modified to provide therapeutic drugs at the site of implantation. That is, a stent can be coated with a polymer impregnated with a drug and, when the stent is in place, the drug elutes from the polymer. A variety of polymers can be used to coat stents. Poly(ethylene-co-vinyl alcohol) (EVAL), is a commercial polymer that has been found to be useful for this purpose.

EVAL possesses desirable coating characteristics such as relative impermeability to oxygen, biocompatibility, and adherence to variety of substrates such as, without limitation, stainless steel. It also, however, has drawbacks such as limited solubility in organic solvents and too great an affinity for water. Its limited solubility requires use of strong polar solvents, such as dimethylacetamide (DMAC) or dimethylsulfoxide (DMSO), to dissolve it. These solvents have high boiling points and are difficult to remove during the drying step of the coating process. EVAL's affinity for water can also be problematic in connection with its use as an effective drug carrier. For example, a commonly used grade of EVAL having about 44 mole percent ethylene groups can absorb 5 mass percent of water. This results in swelling of the polymer, which increases its porosity and, as a result, alters the rate of diffusivity of drugs out of the polymer.

What is needed is a polymer that retains EVAL's favorable characteristics but is more soluble in organic solvents so as to be more amenable to manufacturing and has less of an affinity for water so as to be more useful in the controlled release of drugs in vivo. The present invention provides such polymers.

SUMMARY

Thus in one aspect, this invention relates to a coating for an implantable medical device having the chemical formula:

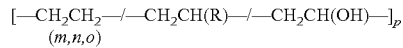
[—CH$_2$CH$_2$—/—CH$_2$CH(R)—/—CH$_2$CH(OH)—]$_p$
(m,n,o)

wherein:

R is selected from a group consisting of alkyl-O—, alkylsulfonyl-O—, alkyl-C(O)O—, —NHR$^1$, phenyl, alkylphenyl, trifluoromethyl, perfluoroalkyl, NH$_2$C(O)—, R$^1$HNC(O)—, R$^1$HNC(O)O— and a macromolecule, wherein:

the alkyl group of the alkyl-O—, alkylsulfonyl-O—, alkyl-C(O)O— or alkylphenyl is unsubstituted, partially fluorinated or fully fluorinated;

R$^1$ is selected from the group consisting of monomethylated poly(ethylene glycol), poly(propylene glycol), poly(vinylpyrrolidone), poly(acrylamide), poly(2-hydroxyethylmethacrylate), a phospholipid, heparin, low molecular weight heparin, a heparinoid, hyaluronic acid and albumin;

the macromolecule is selected from the group consisting of poly(ethylene glycol), poly(propylene glycol), poly(vinylrolidone), poly(acrylamide), poly(2-hydroxyethylmethacrylate), a phospholipid, heparin, low molecular weight heparin, a heparinoid, hyaluronic acid, albumin and a polysiloxane;

m is the mol percent —CH$_2$CH$_2$— in the polymer and is from about 20 to about 80;

n is the mol percent —CH$_2$CH(R)— in the polymer and is from about 1 to about 40;

o is the mol percent —CH$_2$CH(OH)— in the polymer and is (100−(m+n)); and, p is from about 20,000 Da to about 500,000 Da.

In an aspect of this invention, R is selected from the group consisting of (C$_1$-C$_{12}$)alkyl-O—, (C$_1$-C$_{12}$)alkylsulfonyl-O— and (C$_1$-C$_{12}$)alkyl-C(O)O— wherein the alkyl moiety of the group is unsubstituted, partially fluorinated or fully fluorinated.

In an aspect of this invention, R is selected from the group consisting of (C$_1$-C$_6$)alkyl-O—, (C$_1$-C$_6$)alkylsulfonyl-O— and (C$_1$-C$_6$)alkylC(O)O— wherein the alkyl moiety of the group is unsubstituted, partially fluorinated or fully fluorinated.

In an aspect of this invention, R$^1$ is selected from the group consisting of monomethylated poly(ethylene glycol)s.

In as aspect of this invention, the monomethylated poly (ethylene glycol) has a molecular weight of from about 300 Da to about 20,000 Da.

In an aspect of this invention, the macromolecule is poly (dimethylsiloxane).

In an aspect of this invention, the poly(dimethylsiloxane) has a molecular weight of from about 100 Da to about 10,000 Da.

In an aspect of this invention, the macromolecule is poly (ethylene glycol).

In an aspect of this invention, the poly(ethylene glycol) macromolecule has a molecular weight of from about 300 Da to about 20,000 Da.

In an aspect of this invention, the coating further comprises a drug.

In an aspect of this invention, the drug is selected from the group consisting of actinomycin D is also known as dactinomycin, actinomycin IV, actinomycin I$_1$, actinomycin X$_1$, and actinomycin C$_1$; antineoplastics and/or antimitotics such as, without limitation, paclitaxel, docetaxel, methotrexate, azathioprine, vincristine, vinblastine, fluorouracil, doxorubicin hydrochloride, and mitomycin; antiplatelet, anticoagulant, antifibrin, and antithrombin drugs such as, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin, and thrombin; cytostatic or antiproliferative agents such as, without limitation, angiopeptin; angiotensin converting enzyme inhibitors such as captopril, cilazapril or lisinopril; calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide; antiallergic agent such as, without limitation, permirolast potassium; other therapeutic agents such as, without limitation, alpha-interferon, genetically engineered epithelial cells, tacrolimus, clobetasol, dexamethasone and its derivatives, and rapamycin, its derivatives and analogs such as 40-O-(2-hydroxy)ethyl-rapamycin (EVEROLIMUS®), 40-O-(3-hydroxy)propyl-rapamycin, 40-O-[2-(2-hydroxy)ethoxy]ethyl-rapamycin, and 40-O-tetrazole-rapamycin.

In an aspect of this invention, the implantable medical device is selected from the group consisting of a stent, a stent graft, a closure device for a patent formamen ovale, a heart valve, a cerebrospinal fluid shunt, a vascular graft, an arterial puncture closure device and a pacemaker lead.

In an aspect of this invention, the implantable medical device is a stent

In an aspect of this invention, the polymer absorbs 5% or less water by mass.

An aspect of this invention is an implantable medical device comprising a coating comprising a polymer having the above chemical formula.

DETAILED DESCRIPTION

Definitions

As used herein, "$(C_m\text{-}C_n)$" in which m and n are integers refers to the number of carbon atoms in an alkyl, alkenyl, alkynyl and in the ring of a cycloalkyl group. That is, an alkyl, alkenyl, alkynyl or ring of a cycloalkyl can contain from m to n, inclusive, carbon atoms. If no m and n are designated herein, the broadest range described in these definitions is to be assumed. Thus "alkyl" alone means $(C_1\text{-}C_{20})$alkyl. A $(C_1\text{-}C_4)$alkyl, on the other hand refers to all alkyl groups having from 1 to 4 carbons, that is, $CH_3$—, $CH_3CH_2$—, $CH_3CH_2CH_2$—, $CH_3CH(CH_3)$—, $CH_3CH_2CH_2CH_2$—, $CH_3CH_2CH(CH_3)$— and $(CH_3)_3CH$— and a $(C_3\text{-}C_6)$cycloalkyl refers to cyclopropyl, cyclobutyl, cyclopentyl and cyclohexyl.

As used herein, "alkyl" refers to a straight or branched chain fully saturated (no double or triple bonds) hydrocarbon (all carbon backbone) group. An alkyl group of this invention may comprise from 1-20 carbon atoms, that is, m=1 and n=20. It is presently preferred that the alkyl be a $(C_1\text{-}C_{12})$alkyl and presently more preferred that it be a $(C_1\text{-}C_6)$alkyl.

As used herein, "partially fluorinated" refers to a group in which some, but not all, of the hydrogen atoms bonded to carbon atoms of the group are replaced by fluorine atoms. As used herein, as few as one and as many as (h−1) hydrogen atoms, wherein h is the total number of hydrogen atoms bonded to carbon in the group, may be substituted by fluorine and the group is considered to be partially fluorinated.

As used herein, "fully fluorinated" refers to a group in which all of the hydrogen atoms bonded to carbon atoms of the group are replaced by fluorine atoms.

As used herein, "alkenyl" refers to an alkyl group that contains in the straight or branched hydrocarbon chain one or more double bonds.

As used herein, "alkynyl" refers to an alkyl group that contains in the straight or branched hydrocarbon chain one or more triple bonds.

As used herein, "cycloalkyl" refers to a completely saturated (no double bonds) hydrocarbon ring. Cycloalkyl groups of this invention may range from $C_3$ to $C_{10}$, preferably at present from $C_3$ to $C_7$.

As used herein, "aryl" refers to a carbocyclic (all carbon) ring or two or more fused rings (rings that share two adjacent carbon atoms) that have a fully delocalized pi-electron system. Examples of aryl groups include, but are not limited to, phenyl, naphthyl and azulenyl.

As used herein, "alkylsulfonyl" refers to an alkyl-$SO_2$— group.

As used herein, "trifluoromethyl refers to a $F_3C$— group.

As used herein, "perfluoroalkyl" refers to an alkyl group in which all of the hydrogen atoms attached to carbon are substituted with fluorine atoms. Perfluoroalkyl is synonymous with a "fully fluorinated" alkyl.

As used herein, "monomethylated poly(ethylene glycol) refers to a molecule having the general chemical structure $CH_3O$—(—$CH_2CH_2O$—)$_p CH_2CH_2O$—.

As used herein, a "polymer analogous transformation" refers to the chemical transformation of a polymer using organic reactions normally associated with small molecule chemistry but in which at least one of the reactants is a polymer.

As used herein, a compound with the formula [—U—/—V—/—W—/ . . . ] (m, n, o, . . . ) is a polymer in which U, V, W, etc., represent the constitutional units, that is the units derived from each monomer and m, n, o, etc. refers to the molar or simply mol percent of each constitutional unit in order of their appearance in the compound. That is, m is the molar percent of U, n is the molar percent of V, etc. The formula as written, unless expressly stated to be stated, refers to any one of a regular alternating polymer, a random alternating polymer, a regular block polymer, a random block polymer or a purely random polymer. A regular alternating polymer has the general structure, U—V—W—U—V—W—U—V—W— . . . . A random alternating polymer has the general structure, U—V—W—W—U—V—W—U—W—U—V— . . . , it being understood that the exact juxtaposition of the various constitution units may vary. A regular block polymer, with the proviso that the juxtaposition of blocks, the number of constitutional units in each block and the number of blocks may vary, has the general structure, U—U—U—V—V—V—W—W—W— . . . while a random block polymer, with the forgoing provisos still applying, has the general structure, U—U—U—W—W—U—U—V—V—V—V—W—W—W—U—U—W—W—W— . . . .

As used herein, "low molecular weight heparins" refers to fragments of unfractionated heparin. Whereas unfractionated heparin is a heterogeneous mixture of highly sulfated polysaccharide chains ranging in molecular weight from about 3,000 to about 30,000 DA, low molecular weight heparins have a molecular weight between about 4,000 and about 6,000 DA. The term "low molecular weight heparins" and the molecules to which the term refers are well-known to those skilled in the medical arts.

As used herein, "heparinoids" refers to naturally-occurring and synthetic highly sulfated polysaccharides that are structurally similar to heparin. Examples, without limitation, of heparinoids are danaparoid sodium, fondaparinux and idraparinux. As with low molecular weight heparins, heparinoids are well-known to those skilled in the medical arts.

DISCUSSION

The present invention relates to modified EVAL polymers that can be used in conjunction with one or more drugs such that, when the polymer is coated on implantable medical device and the device is implanted in a patient, the polymer will participate in the controlled release the drug(s) at the site of implantation. The EVAL is modified to retain its desirable characteristics and to reduce or eliminate those characteristics that are less desirable. That is, without limitation, biocompatibility, imperviousness to oxygen and adhesion are maintained while organic solvent solubility is improved and water absorption reduced. Modification of EVAL is accomplished by either polymer-analogous transformation or by ab initio co-polymerization of ethylene, vinyl acetate (which is eventually hydrolyzed to provide the vinyl alcohol portion of the polymer) and one or more additional vinyl monomers selected to confer the desired characteristics on the resultant polymeric product.

The amount of modified vinyl alcohol in a polymer of this invention can be from about 1 mol percent to about 40 mol percent, preferably 1 mol percent to about 25 mol percent and presently most preferably from about 2 mol percent to about 10 mol percent.

The polymer can be coated onto the implantable medical device by methods known to those of ordinary skill in the art such as, without limitation, spraying, electrospraying, dipping, molding, roll coating, spin coating, direct dispense and piezoelectric droplet dispense. A drug may be incorporated into the coating, applied as a separate layer beneath the coating, or adsorbed onto the surface of the coating. The polymer may also be used as a primer layer on the implantable medical device to assist in the adhesion of subsequent layers and/or as a topcoat layer to protect the layers under it.

Any type of implantable device can be coated with a polymer of this invention. An implantable medical device so coated can be used anywhere in the body where such devices are normally employed. In particular at present, implantable devices such as those designed for use in the core or peripheral vascular system including, without limitation, the neurological, carotid, coronary, renal, aortic, iliac or femoral vasculature can be used. For example, without limitation, the implantable device may be a self-expandable stent, a balloon-expandable stent, a stent-graft, an artificial heart valve, a cerebrospinal fluid shunt, a coronary shunt, a pacemaker electrode or an endocardial lead (e.g., FINELINE and ENDOTAK, available from Guidant Corporation). The implantable medical device can be of virtually any design and made of any material presently known or as may be developed in the future for such use. For example, without limitation, currently available implantable medical devices can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from biocompatible, bio-absorbable and/or bio-stable polymers can also be coated with the polymers of this invention.

Drugs that may be used with the coatings of this invention include, without limitation:

antiproliferative drugs such as actinomycin D, or derivatives or analogs thereof. Actinomycin D is also known as dactinomycin, actinomycin IV, actinomycin $I_1$, actinomycin $X_1$, and actinomycin $C_1$;

antineoplastics and/or antimitotics such as, without limitation, paclitaxel, docetaxel, methotrexate, azathioprine, vincristine, vinblastine, fluorouracil, doxorubicin hydrochloride, and mitomycin;

antiplatelet, anticoagulant, antifibrin, and antithrombin drugs such as, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin, and thrombin;

cytostatic or antiproliferative agents such as, without limitation, angiopeptin; angiotensin converting enzyme inhibitors such as captopril, cilazapril or lisinopril; calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide;

antiallergic agent such as, without limitation, permirolast potassium.

other therapeutic agents such as, without limitation, alpha-interferon, genetically engineered epithelial cells, tacrolimus, clobetasol, dexamethasone and its derivatives, and rapamycin, its derivatives and analogs such as 40-O-(2-hydroxy)ethyl-rapamycin (EVEROLIMUS®), 40-O-(3-hydroxy)propyl-rapamycin, 40-O-[2-(2-hydroxy)ethoxy]ethyl-rapamycin, and 40-O-tetrazole-rapamycin.

Synthesis

The following synthetic routes to polymers of this invention are provided by way of illustration only and are not intended nor are they to be construed as limiting the scope of this invention in any manner whatsoever.

EVAL Modification by Polymer-Analogous Transformation (Alkylation)

Alkylation of the hydroxyl of the vinyl alcohol constitutive units of EVAL reduces intra- and inter-molecular hydrogen bonding, thus improving the solubility of the polymer in organic solvents and reducing the tendency of the polymer to absorb water and expand. Polymer analogous alkylation may be carried out by any means known to those skilled in the art such as, without limitation, the reaction of the polymer with an alkyl halide in the presence of base:

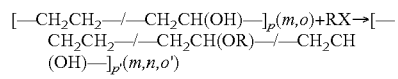

wherein R is an alkyl group that may be unsubstituted, partially fluorinated or fully fluorinated and X is chlorine, bromine, or iodine. Integers m, n, o and o' represent the mol percent of each constitutional element of the starting EVAL and the modified EVAL product. The integer m is from about 20 to about 80 mol percent of the starting EVAL and o is (100−m). The integer n is from about 1 mol percent to about 40 mol percent, preferably at present from about 1 mol percent to about 25 mol percent and, at present, most preferably from about 2 to about 10 mol percent. The integer o' is then (100−(m+n)). The integer p represents the average molecular weight of the starting EVAL and is at present preferably between about 20,000 Da and about 500,000 Da. The integer p' represents the molecular weight of the modified EVAL product and will be approximately (p+the molecular weight of R times the average number of R units in a molecule of the modified EVAL).

Any method of alkylation that results in alkylation of the hydroxyl group of the vinyl alcohol moieties of EVAL can be used and all such methods are within the scope of this invention. For example, in addition to the above reaction, EVAL can be alkylated with, without limitation, alkyl sulfates in the presence of base, diazomethane in the presence of a Lewis acid such as, without limitation, $HBF_4$ or $BF_3$ to form the methyl derivative or by an olefin in the presence of a strong acid.

The alkylated EVAL will be more-hydrophobic than the parent EVAL and more soluble in organic solvents which should provide drug-containing coatings for implantable medical devices that exhibit improved drug-releasing characteristics.

EVAL Modification by Polymer-Analogous Transformation (Fluoroalkyl-Sulfonylation)

EVAL can be fluoroalkylsulfonyated by reaction with the appropriate fluoroalkylsulfonyl halide in the presence of a base:

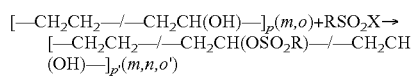

wherein R an alkyl group that may be unsubstituted, partially fluorinated or fully fluorinated, X is chlorine, bromine or iodine. The integers m, n, o, o', p and p' have the same meaning as above.

As the fluorine content of the modified EVAL increases, the polymer's ability to adhere to certain materials such as, without limitation stainless steel may be adversely affected; thus, an appropriate balance between the increase in organic solvent solubility and reduction in hydrophilicity and reduction in adhesion must be achieved. Those skilled in the art will be able to determine such balances of characteristics without undue experimentation and all such compositions of the modified EVAL are within the scope of this invention.

EVAL Modification by Polymer-Analogous Transformation (Silylation)

EVAL can be modified using low molecular weight oligomers of poly(dimethylsiloxane) (PDMS). Such functionalization should provide EVAL with improved hydrophobicity, surface inertness and blood compatibility. Modification of EVAL to introduce silicon groups may be carried out, without limitation, by the reaction with a commercially available epoxy-terminated PDMS:

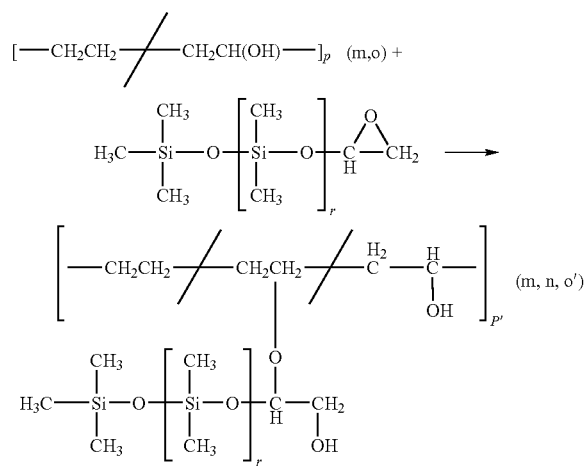

The reaction is generally carried out in the presence of an acid that protonates the epoxide. It is presently preferred that the siloxane oligomer have a molecular weight of from about 300 to about 3,000 Daltons, that is, r, which represents the number of repeating units in the oligomer is from about 4 to about 40. The integers m, n, o, o', p and p' have the same meaning as previously indicated herein.

As with the fluoroalkylation and fluoroalkylsulfonylation, if the degree of functionalization is too high, adhesion of the polymer to an implantable medical device may be adversely affected so an appropriate balance among solubility in organic solvents, reduced hydrophilicity and adhesion to an implantable device must be achieved. Again, determining the appropriate balance can be accomplished by those skilled in the art without undue experimentation based on the disclosure herein and all such component-balanced polymers are within the scope of this invention.

EVAL Modification by Polymer-Analogous Transformation (Esterification)

The vinyl alcohol group of EVAL can be esterified by methods well-known to those skilled in the art. For example, without limitation, EVAL can be esterified using an acyl halide or an anhydride in a solvent such as, without limitation, dimethylacetamide, in the presence of a base such as, again without limitation, triethylamine:

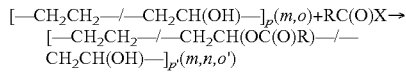

In the above reaction, R is an alkyl group as defined herein. The alkyl group may be unsubstituted, partially fluorinated or fully fluorinated. X is a leaving group such as, without limitation, chlorine or bromine. X can also be RC(O)O— in which case RC(O)X is an acid anhydride. Numerous other leaving groups and reactants in general useful for esterification will become apparent to those skilled in the art based on the disclosures herein; all such leaving groups and reactants are within the scope of this invention. The integers m, n, o, o', p and p' have the same meaning as previously indicated.

EVAL Modification by Polymer-Analogous Transformation (Reaction with PEG)

EVAL can be reacted with poly(ethylene glycol) (PEG), a process often referred to as "PEGylation," to provide in essence a graft copolymer:

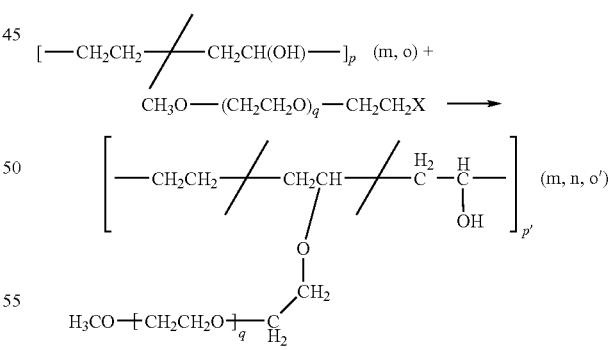

Poly(ethylene glycol) (PEG), which has the general chemical formula HO—$[CH_2—CH_2—O]_n$—H is usually monomethylated (as shown) prior to functionalization and reaction with other moieties. The monomethyl derivative, known as MPEG, can be obtained by, without limitation, anionic ring opening polymerization of ethylene oxide initiated by methoxide anion ($CH_3O^-$). The remaining terminal hydroxyl group can then be converted to an efficient leaving group that will react with the hydroxy anion of EVAL, which can be formed by reaction with a strong base such as, without limitation, t-butoxide. On the other hand, the hydroxyl group of EVAL can first be converted to a leaving group, as is discussed below with regard to reaction of EVAL with PEG-A, and then the functionalized EVAL can be reacted with the anion of the terminal hydroxyl group of MPEG. In the above reaction sequence, m, n, o, o', p and p' have the meanings described previously. The integer q represents the number of repeating units of —$CH_2CH_2O$— groups in the MPEG. The integer q can be from about 300 DA to about 20,000 Da.

EVAL Modification by Polymer-Analogous Transformation (Reaction with PEG-A)

A poly(ethylene glycol)-amine adduct (PEG-A) such as, without limitation, $CH_3O$—[—$CH_2$—$CH_2O$]$_q$—$CH_2CH_2NH_2$ can be used to modify EVAL. In the PEG-A, the integer q is the number of —$CH_2CH_2O$— constitutional units in the PEG-A and can be from about 7 to about 227, corresponding to a molecular weight of from about 300 Da to about 10,000 Da.

To prepare EVAL/PEG adducts, the vinyl alcohol hydroxyl groups of EVAL are first converted into leaving groups by methods well-known to those skilled in the art. For example, without limitation, the hydroxyl groups can be reacted with tosyl chloride, $CH_3$—$C_6H_4$—$SO_2Cl$, in the presence of a base such as, without limitation, triethylamine to form the tosylate ester, $CH_3$—$C_6H_4$—$SO_2$—O-EVAL in which toluene sulfonic acid, $C_6H_4$—$SO_2OH$, is a facile leaving group. Reaction of the tosylate with the free amine of PEG-A affords the desired adduct. Another example of a leaving group is the tresylate ester of EVAL, $CF_3$—$CH_2SO_2$O-EVAL, which is obtained by the reaction of vinyl alcohol groups of EVAL with tresyl chloride, $CF_3$—$CH_2SO_2Cl$. As noted above, many such leaving groups will be apparent to those skilled in the art based on the disclosures herein and all such leaving groups and their reactions are within the scope of this invention.

In an aspect of this invention, the hydroxyl groups of EVAL may be activated with carbonyl diimidazole. Subsequent reaction of the derivatized EVAL with monomethylated poly(ethylene glycol) amine ($mPEGNH_2$) gives an mPEG-EVAL conjugate linked by a urethane moiety.

EVAL Modification by Copolymerization Using Alkylated Monomer

The same alkylated EVAL prepared above by polymer analogous transformation may also be prepared by copolymerization of ethylene, vinyl acetate and the appropriate vinyl ether, followed by the hydrolysis of the vinyl acetate moieties.

Co-polymerization can be carried out by any method known to those skilled in the art. For example, without limitation, free radical polymerization using azo-bis-isobutyrylnitrile (AIBN) as a catalyst may be used.

EXAMPLES

Example 1

Fabrication of Polymer-Coated Implantable Medical Device

Primer Layer

Poly(ethylene-co-vinyl alcohol) (44 mol percent ethylene/56 mol percent vinyl alcohol) is dissolved in a 1:1 DMSO:DMAC (by weight) to give a 2% by weight solution. An EFD 780S spray nozzle with a VALVEMATE 7040 control system, manufactured by EFD, Inc., East Providence, R.I. is used to spray the polymer solution onto a stent. During the process of applying the composition, the stent can be optionally rotated about its longitudinal axis, at a speed of 50 to about 150 rpm. The stent can also be linearly moved along the same axis during the application.

The 2% solution of the polymer is applied to a 13-mm TETRA stent (available from Guidant Corporation) in a series of 10-second passes, to deposit 10 μg of coating per spray pass. Between the spray passes, the stent is dried for 10 seconds using a flow of air at 80° C. Five spray passes are applied to form a 50 μg primer layer, followed by baking the primer layer at 140° C. for one hour.

Drug-Containing Layer

A mixture is prepared that consists of, by weight, 2% of poly(ethylene-co-butyl vinyl ether-co-vinyl alcohol) (44 mol percent ethylene/10 mol percent butyl vinyl ether/46 mol percent vinyl alcohol), 1.33% of Everolimus, a derivative of rapamycin, and 96.67% of the 1:1 (by weight) DMSO:D-MAC. The same apparatus used to spray the primer layer on the stent is used to apply the drug layer: seventy spray passes are performed to form a 700 μg drug-polymer layer, followed by drying the drug-polymer layer at 50° C. for 2 hours.

Topcoat Layer

A topcoat layer comprising, by weight, 2% of poly(ethylene-co-butyl vinyl ether-co-vinyl alcohol) (44 mol percent ethylene/10 mol percent butyl vinyl ether/46 mol percent vinyl alcohol) and 98% of 4:1 DMAC:pentane is then applied over the drug-containing layer using the same apparatus used to coat the primer layer and the drug-containing layer. Fifteen spray passes are performed to form a 150 μg topcoat layer, followed by drying at 50° C. for 2 hours.

Finish Coat Layer

A finish coat layer comprising, by weight, 2% of poly(ethylene-co-mPEG(560)urethane-co-vinyl alcohol) (44 mol percent ethylene/3 mol percent mPEG(560)urethane/53 mol percent vinyl alcohol) and 98% of 5:3:2 DMAC:ethanol:DMSO. In a manner identical to the application of the previous three layers, thirty-five spray passes are performed to form a 350 μg finishing coat layer, followed by drying at 50° C. for 2 hours.

While particular embodiments of the present invention have been described above, it will be obvious to those skilled in the art that changes and modifications can be made without departing from the scope of this invention. Such changes and modifications are within the scope of this invention.

What is claimed:

1. A coating for an implantable medical device comprising a polymer having the chemical formula:

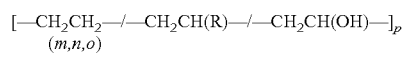
$(m,n,o)$ wherein:
R is selected from a group consisting of alkyl-O—, alkylsulfonyl-O—, $NHR^1$, phenyl, alkylphenyl, trifluoromethyl, perfluoroalkyl, $R^1HNC(O)$—, $R^1HNC(O)O$— and a macromolecule, wherein:
the alkyl group of the alkyl-O—, or alkylsulfonyl-O— is unsubstituted, partially fluorinated or fully fluorinated;
$R^1$ is selected from the group consisting of monomethylated poly(ethylene glycol), poly(propylene glycol), poly(vinylpyrrolidone), poly(acrylamide), poly(2-hydroxyethylmethacrylate), a phospholipid, heparin, low molecular weight heparin, a heparinoid, hyaluronic acid and albumin;

the macromolecule is selected from the group consisting of poly(ethylene glycol), poly(propylene glycol), poly(vinylpyrrolidone), poly(acrylamide), poly(2-hydroxyethylmethacrylate), a phospholipid, heparin, low molecular weight heparin, a heparinoid, hyaluronic acid, albumin and a polysiloxane;

m is the mol percent $CH_2CH_2$— in the polymer and is from about 20 to about 80;

n is the mol percent $CH_2CH(R)$— in the polymer and is from about 1 to about 40;

o is the mol percent $CH_2CH(OH)$— in the polymer and is (100−(m+n)); and, p is from about 20,000 Da to about 500,000 Da.

2. The coating of claim 1, wherein R is selected from the group consisting of $(C_1-C_{12})$alkyl-O— and $(C_1-C_{12})$alkylsulfonyl-O— wherein the alkyl moiety of the group is unsubstituted, partially fluorinated or fully fluorinated.

3. The coating of claim 1, wherein R is selected from the group consisting of $(C_1-C_6)$alkyl-O—, and $(C_1-C_6)$alkylsulfonyl-O— wherein the alkyl moiety of the group is unsubstituted, partially fluorinated or fully fluorinated.

4. The coating of claim 1, wherein $R^1$ is selected from the group consisting of monomethylated poly(ethylene glycol)s.

5. The coating of claim 4, wherein the monomethylated poly(ethylene glycol) has a molecular weight of from about 300 Da to about 20,000 Da.

6. The coating of claim 1, where the macromolecule is poly(dimethylsiloxane).

7. The coating of claim 6, wherein the poly(dimethylsiloxane) has a molecular weight of from about 100 Da to about 10,000 Da.

8. The coating of claim 1, wherein the macromolecule is monomethylated poly(ethylene glycol).

9. The coating of claim 8, wherein the monomethylated poly(ethylene glycol) has a molecular weight of from about 300 Da to about 20,000 Da.

10. The coating of claim 1, further comprising a drug.

11. The coating of claim 10, wherein the drug is selected from the group consisting of actinomycin D; antineoplastics and/or antimitotics such as, without limitation, paclitaxel, docetaxel, methotrexate, azathioprine, vincristine, vinblastine, fluorouracil, doxorubicin hydrochloride, and mitomycin; antiplatelet, anticoagulant, antifibrin, and antithrombin drugs such as, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin, and thrombin; cytostatic or antiproliferative agents such as, without limitation, angiopeptin; angiotensin converting enzyme inhibitors such as captopril, cilazapril or lisinopril; calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide; antiallergic agent such as, without limitation, permirolast potassium; other therapeutic agents such as, without limitation, alpha-interferon, genetically engineered epithelial cells, tacrolimus, clobetasol, dexamethasone and its derivatives, and rapamycin, its derivatives and analogs such as 40-O-(2-hydroxy)ethyl-rapamycin (EVEROLIMUS®), 40-O-(3-hydroxy)propyl-rapamycin, 40-O-[2-(2-hydroxy)ethoxy]ethyl-rapamycin, and 40-O-tetrazole-rapamycin.

12. The coating of claim 1, wherein the implantable medical device is selected from the group consisting of a stent, a stent graft, a closure device for a patent formamen ovale, a heart valve, a cerebrospinal fluid shunt, a vascular graft, an arterial puncture closure device and a pacemaker lead.

13. The coating of claim 12, wherein the implantable medical device is a stent.

14. The coating of claim 1, wherein the polymer absorbs 500 or less water by weight.

* * * * *